(12) United States Patent
Padova

(10) Patent No.: US 7,833,183 B2
(45) Date of Patent: Nov. 16, 2010

(54) FUNCTIONAL LOW-PROFILE DYNAMIC EXTENSION SPLINT AND METHODS FOR ITS USE AND MANUFACTURE

(75) Inventor: Joseph R. Padova, Philadelphia, PA (US)

(73) Assignee: Albert Einstein Healthcare Network, Philadelphia, PA (US)

( * ) Notice: Subject to any disclaimer, the term of this patent is extended or adjusted under 35 U.S.C. 154(b) by 149 days.

(21) Appl. No.: 11/845,485

(22) Filed: Aug. 27, 2007

(65) Prior Publication Data

US 2009/0062708 A1  Mar. 5, 2009

(51) Int. Cl.
*A61F 5/00* (2006.01)

(52) U.S. Cl. .............................. 602/22; 602/5; 602/20; 602/21

(58) Field of Classification Search ............ 602/5, 602/20, 21, 22; 128/878–881; 482/48, 47; 601/40
See application file for complete search history.

(56) References Cited

U.S. PATENT DOCUMENTS

| | | | | |
|---|---|---|---|---|
| 897,471 | A * | 9/1908 | Loyola | 482/48 |
| 1,389,741 | A * | 9/1921 | Cotton | 602/21 |
| 1,708,757 | A * | 4/1929 | Freileweh | 602/20 |
| 2,237,251 | A * | 4/1941 | Longfellow | 602/22 |
| 4,438,532 | A * | 3/1984 | Campanella et al. | 2/16 |
| 4,456,002 | A | 6/1984 | Barber et al. | |
| 4,602,620 | A | 7/1986 | Marx | |
| 4,765,320 | A | 8/1988 | Lindemann et al. | |
| 4,790,301 | A | 12/1988 | Silfverskiold | |
| 4,807,606 | A | 2/1989 | Hasegawa et al. | |
| 4,949,711 | A | 8/1990 | Gyovai et al. | |
| 5,027,802 | A | 7/1991 | Donohue | |
| 5,103,807 | A | 4/1992 | Makaran | |
| 5,178,137 | A | 1/1993 | Goor | |
| 5,183,458 | A | 2/1993 | Marx | |
| 5,267,945 | A | 12/1993 | Doctor et al. | |
| 5,324,251 | A | 6/1994 | Watson | |
| 5,346,462 | A | 9/1994 | Barber | |
| RE34,753 | E | 10/1994 | Groiso | |
| 5,376,091 | A | 12/1994 | Hotchkiss et al. | |
| 5,409,447 | A | 4/1995 | Wedge, Jr. | |
| 5,413,554 | A | 5/1995 | Trueman | |
| D373,639 | S | 9/1996 | McKie | |
| 5,876,363 | A * | 3/1999 | Marx | 602/21 |
| 6,502,577 | B1 * | 1/2003 | Bonutti | 128/898 |
| 6,520,925 | B1 * | 2/2003 | Thibodo, Jr. | 602/22 |
| 6,561,995 | B1 * | 5/2003 | Thibodo, Jr. | 602/22 |
| 6,565,563 | B1 | 5/2003 | Agee et al. | |
| 6,849,056 | B1 | 2/2005 | Wiggins et al. | |
| 6,921,377 | B2 | 7/2005 | Bonutti | |

(Continued)

OTHER PUBLICATIONS

"Sammons Preston Catologue Entries" dated Aug. 7, 2007.

(Continued)

*Primary Examiner*—Kim M Lewis
(74) *Attorney, Agent, or Firm*—Niels Haan; Dann Dorfman Herrell & Skillman, PC

(57) ABSTRACT

The present invention relates to medical devices and methods useful for improving a person's ability to grasp and release an object, and more specifically, the present invention relates to a splint for causing dynamic extension of a finger and/or thumb.

24 Claims, 17 Drawing Sheets

U.S. PATENT DOCUMENTS

| | | | |
|---|---|---|---|
| 6,932,782 | B2 | 8/2005 | Ferraioli |
| 6,953,441 | B2 | 10/2005 | Goumas |
| 7,001,352 | B2 | 2/2006 | Farrell et al. |
| 7,135,006 | B1 * | 11/2006 | Weber et al. .................. 602/22 |
| 7,156,819 | B2 | 1/2007 | Sieller et al. |
| 7,169,121 | B2 | 1/2007 | Berrehail |
| D558,883 | S | 1/2008 | Ortiz |
| 2006/0094989 | A1 | 5/2006 | Scott et al. |
| 2006/0149180 | A1 | 7/2006 | Phelen |
| 2006/0211964 | A1 * | 9/2006 | Farrell et al. .................... 602/5 |
| 2006/0247102 | A1 * | 11/2006 | Kupferman .................. 482/44 |
| 2006/0276735 | A1 | 12/2006 | Phelen et al. |

OTHER PUBLICATIONS

"Sammons Preston Catalogue Entries" dated 2009.

Health Industry Products: Hand Therapy, pp. 1-26 dated Jul. 19, 2007 from website printout http://www.opchealth.com.au/hand%20therapy.html.

* cited by examiner

FUNCTIONAL LOW-PROFILE DYNAMIC EXTENSION SPLINT AND METHODS FOR ITS USE AND MANUFACTURE

FIELD OF THE INVENTION

The present invention relates to medical devices and methods useful for improving a person's ability to grasp and release an object. More specifically, the present invention relates to apparatuses for causing dynamic extension of a finger and/or thumb.

BACKGROUND OF THE INVENTION

Many individuals suffer from a condition known as flexor spasticity which prevents the normal extension of the fingers or thumb. Often caused by a stroke, muscular damage, brain damage, nerve damage or degeneration, a person or individual afflicted with flexor spasticity may have difficulty relaxing the muscles that close the hand and contracting the extensor muscles of the digits and thumb, and as a result, the individual may not be able to fully open his or her hand, and may have difficulty grasping and releasing an object.

The majority of dynamic extension splints on the market are designed to be used for post-surgical treatment to provide a slow progressive stretch to the flexor tendons, muscles, or other soft tissues as post-surgical treatment. These existing dynamic extension splints contain high profile outriggers and typically use rubber bands, straps, or exposed springs to provide the dynamic extension. These rubber bands frequently break and need replacement. Additionally, the majority of dynamic extension splints are bulky and are not intended for functional, everyday use. Dynamic extension splints are frequently custom made in the clinic, but some may be purchased through hand rehabilitation and durable medical equipment (DME) catalogues, such as the Saeboflex® dynamic finger and thumb extensor splint. Accordingly, it would be an advance in the state of the art to provide a functional, low-profile, dynamic extension splint for biasing an individual's fingers in an open position to permit the individual to grasp an object and engage in related everyday activities.

SUMMARY OF THE INVENTION

To improve upon the shortcomings of prior art splints, methods and apparatuses useful for treating individuals having flexor spasticity are presented. These methods and apparatuses may be used for treatment or as a supplement to an individual's active daily life (ADL). Methods of using and constructing the apparatus are presented including techniques for customizing the shape and size of the splint for a particular individual.

In one of its aspects, the present invention provides, inter alia, a durable, inexpensive, and low-profile solution to designing a splint capable of extending an individual's fingers. In another of it aspects, the present invention provide splint configurations that do not utilize springs, wires, or rubber bands/straps to create the biasing force required to extend the patient's finger(s). Rubber bands and springs can break or loose their elasticity over time, and often require frequent adjustments. In addition, should one of these parts break, the device may become inoperable which is inconvenient to the individual. Thus, to increase the durability of the dynamic extension splint, configurations of the present invention are disclosed that do not utilize springs, wires, or rubber straps.

In yet another of the aspects of the present invention, minimizing the cost of the device is also an important consideration, and the present invention discloses several low-cost configurations. For example, multiple configurations of the present invention may be constructed using only four separate components (not counting any adhesive or fixating materials). Additionally, patient evaluation has demonstrated that wearing bulky splints or braces can be awkward and socially embarrassing. Moreover, the additional height (thickness) of many prior art devices makes maneuvering one's hand more difficult. To meet these shortcomings a low-profile splint was designed to minimize the impact on the person's physical and social life. Clinical experimental trials of the dynamic extension splint has shown the splint to be effective in training individuals to grip objects as thin as a piece of paper as well as objects over 3½ inches thick. After the first treatment session many individuals were able to stabilize a cup while filling it with water, hold the edges of a coat while zippering or buttoning it, and even tie a bow.

In one of its configurations, the present invention provides a dynamic extension splint for biasing a person's fingers in an open position and having a low-profile configuration. The splint may include a glove having a thumb jacket for positioning the person's thumb by covering and securing a portion of the thumb. The thumb jacket may have elastic properties which assist with opening the thumb thereby aiding in the grasp and release of an object. Optionally, the glove may include a handwrap for securing the glove to the person's hand. A platform may also be included for attachment to the glove. The platform may be configured to rest on the dorsum of the hand and may have an outrigger mount portion to which an outrigger is attached. The splint may also include a flexible outrigger for biasing at least two of a person's fingers in an open position. The flexible outrigger may be mounted to the outrigger mount portion and may extend away from the outrigger mount portion parallel and proximate to the plane of the outrigger mount portion to provide the low-profile configuration of the dynamic extension splint. Two finger extenders may also be provided, each of which may be configured to surround a respective one of the person's index finger and long finger for biasing the fingers into an extended position. The finger extenders may include an arcuate shape designed to fit snuggly around the person's fingers.

In an additional aspect of the present invention, various manufacturing methods for the components of the splint are presented. Additionally, methods for using the splint are disclosed, as well as various methods for customizing the size and shape of the splint for a particular user. Also various methods for selecting a component having specific attributes, such as the rigidity of the rod, are presented.

DETAILED DESCRIPTION OF THE INVENTION

Figure 1:
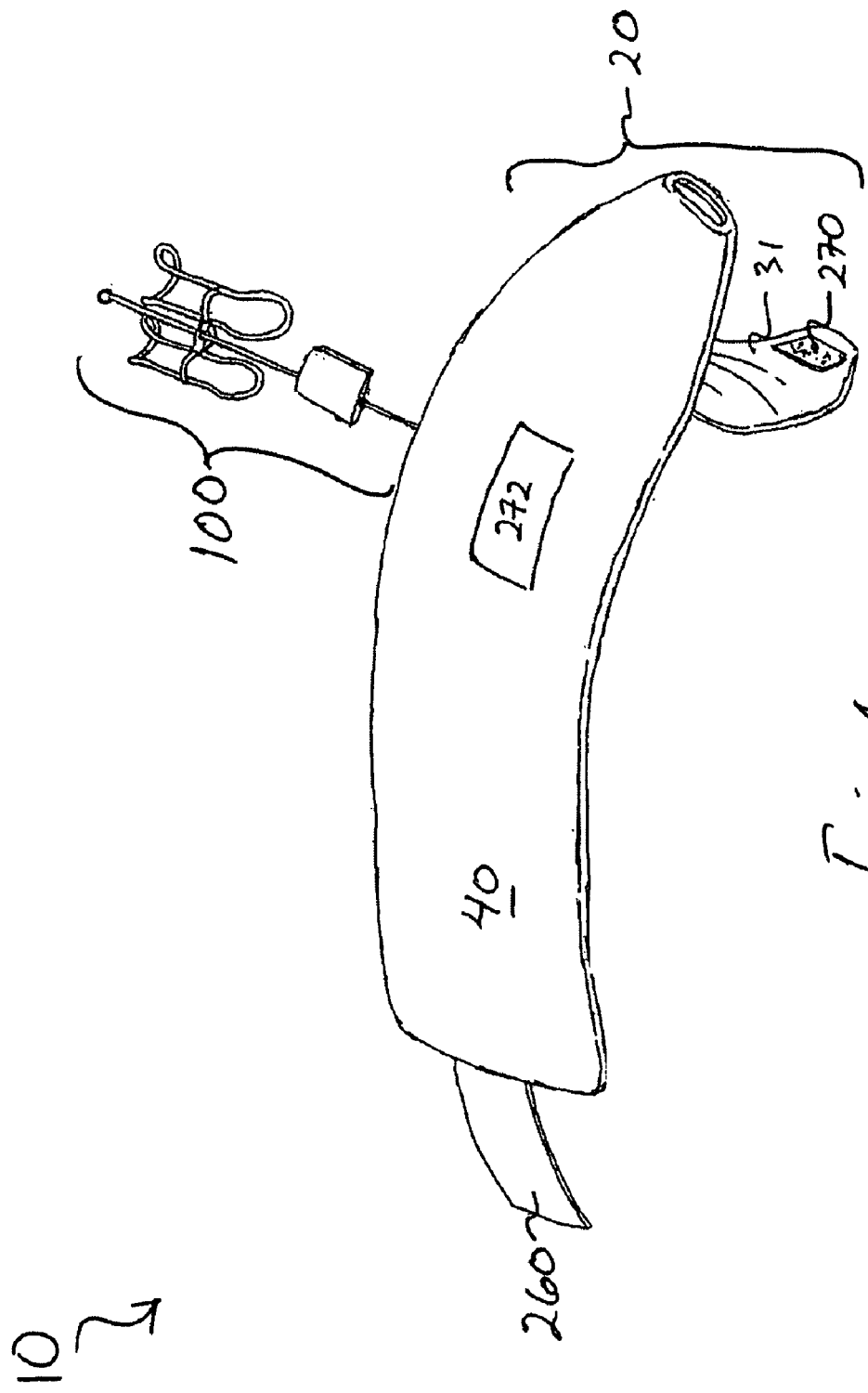
FIG. 1 schematically illustrates a perspective view of a left-handed splint comprising a glove and an extension assembly.

Referring now to the figures, wherein like elements are numbered alike throughout, an exemplary low-profile dynamic extension splint in accordance with the present invention, generally designated "10", is provided, FIG. 1. The dynamic extension splint 10 may comprise a glove 20 and an extension assembly 100 which provide an extension force to bias an individual's fingers and thumb in an open position, which may be particularly helpful to individuals who suffer from flexor spasticity which prevents the normal extension of the fingers through the DIP (distal interphalangeal) and PIP (proximal interphalangeal) joints, FIG. 17. In addition, the dynamic extension splint 10 is sufficiently flexible to allow the individual to bend one or more of their fingers at the knuckle towards the thumb to permit a grip, such as tripod grip, to be formed between the fingers and the thumb, FIG. 18.

Returning to FIG. 1, the splint 10 may include various types of structures for covering and supporting the hand. For example, the overall structure of the splint 10 may take the form of a glove 20, which may include finger coverings, partial finger coverings (like a weightlifting glove), or no finger coverings at all (i.e., a fingerless glove). The glove 20 desirably includes a thumb jacket 32 into which the individual's thumb is placed and an optional thumb hole 30 at the tip of the thumb jacket 32 through which the tip of the thumb may extend. In addition, the glove 20 may include a handwrap 40 for wrapping around the individual's hand and may include an optional hook-and-loop strap 260 for attachment to an optional hook-and-loop pad 272 for securing the handwrap 40 to the individual's hand once the handwrap 40 has been wrapped around the hand. In addition, the glove 20 may optionally include a hook-and-loop pad 270 disposed on a thumb flap 31 for engagement with the underside 33 of the glove 20 once the handwrap 40 has been wrapped around the hand, FIGS. 2, 14. The glove 20 may be composed of materials such as leather or Gore-Tex™ fabric (a fiber made from polytetrafluoroethylene (PTFE)), for example. Depending on the individual's condition, a resilient material capable of returning to its initial shape after being deformed may be selected, such as Neoprene® elastomer (a polychloroprene synthetic rubber manufactured by DuPont Performance Elastomers).

Figure 9:
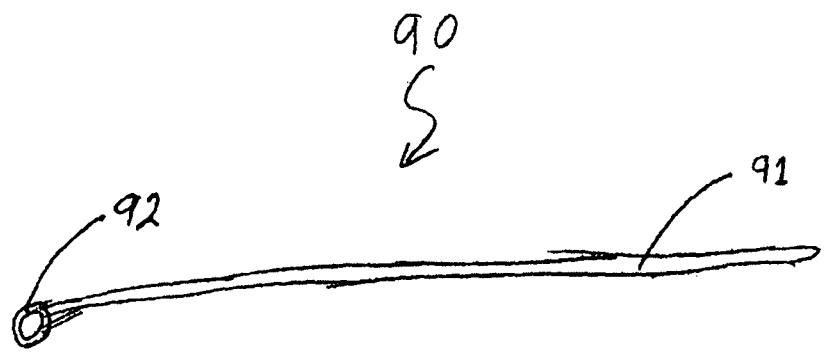
FIG. 9 schematically illustrates a perspective view of the outrigger without the other components of the splint.

The splint 10 also includes an extension assembly 100 attached to the glove 20 for providing a biasing and extension force to the individual's fingers. The extension assembly 100 includes one or more finger extenders 200 attached to an outrigger 90 which in turn is attached to a platform 50 attached to the handwrap 40 of the glove 20, FIG. 2. The outrigger 90 may comprise a rod 91 and a stop 92 disposed at the distal end of the rod 91, which may be shorter or longer than the fingers of the individual, FIG. 9. The rod 91 may be formed from any material having suitable flexibility and resiliency, such as fiberglass or graphite, for example. Typical diameters of the rod 91 can vary from 0.05 to 0.075 inches for fiberglass rods, and from 0.050 to 0.10 inches for graphite rods, for example, but other thicknesses or materials could be used depending on the desired flexibility, rigidity, or resiliency required.

Figure 8:
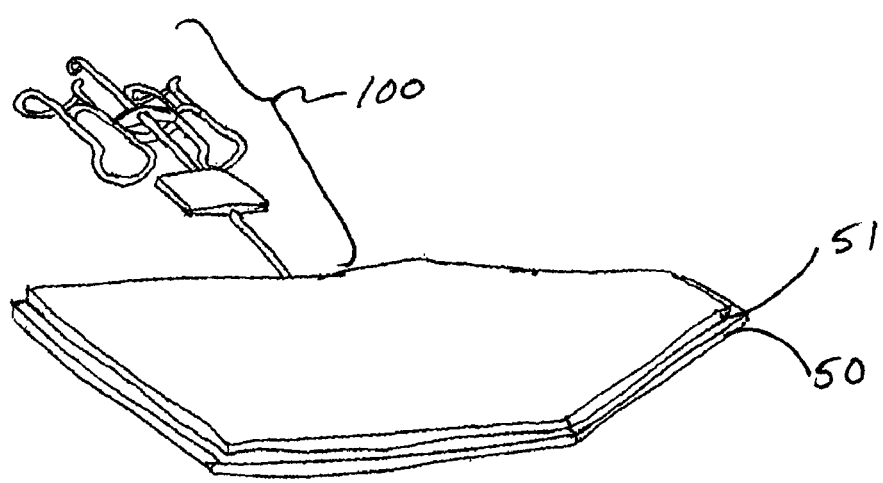
FIG. 8 schematically illustrates a perspective view of the top side of the extension assembly and platform with an optional platform pad attached.
Figure 15:
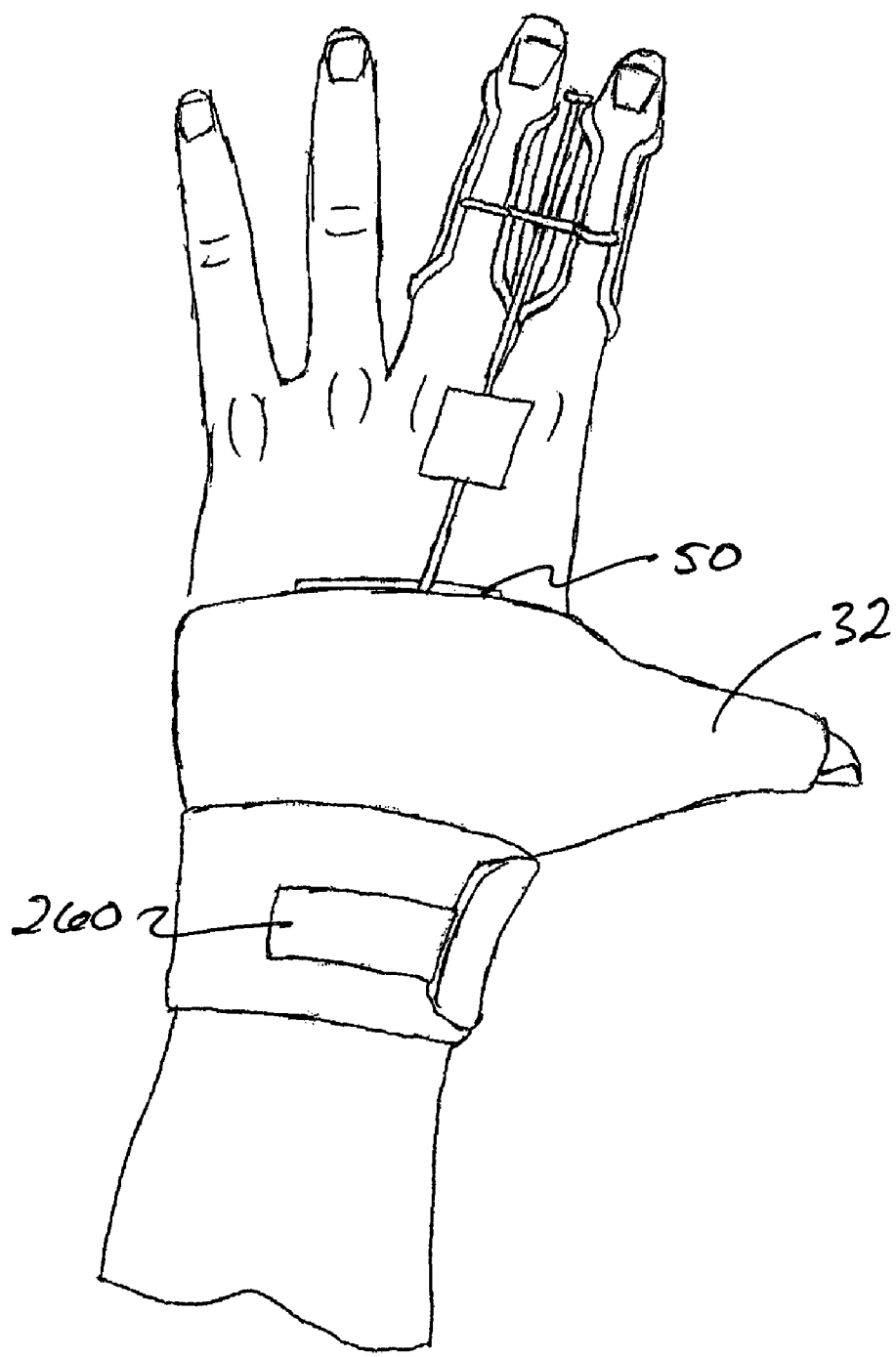
FIG. 15 schematically illustrates a top view of the splint mounted on the person's left hand showing the dorsal side of the hand with the handwrap in a closed position.
Figure 16:
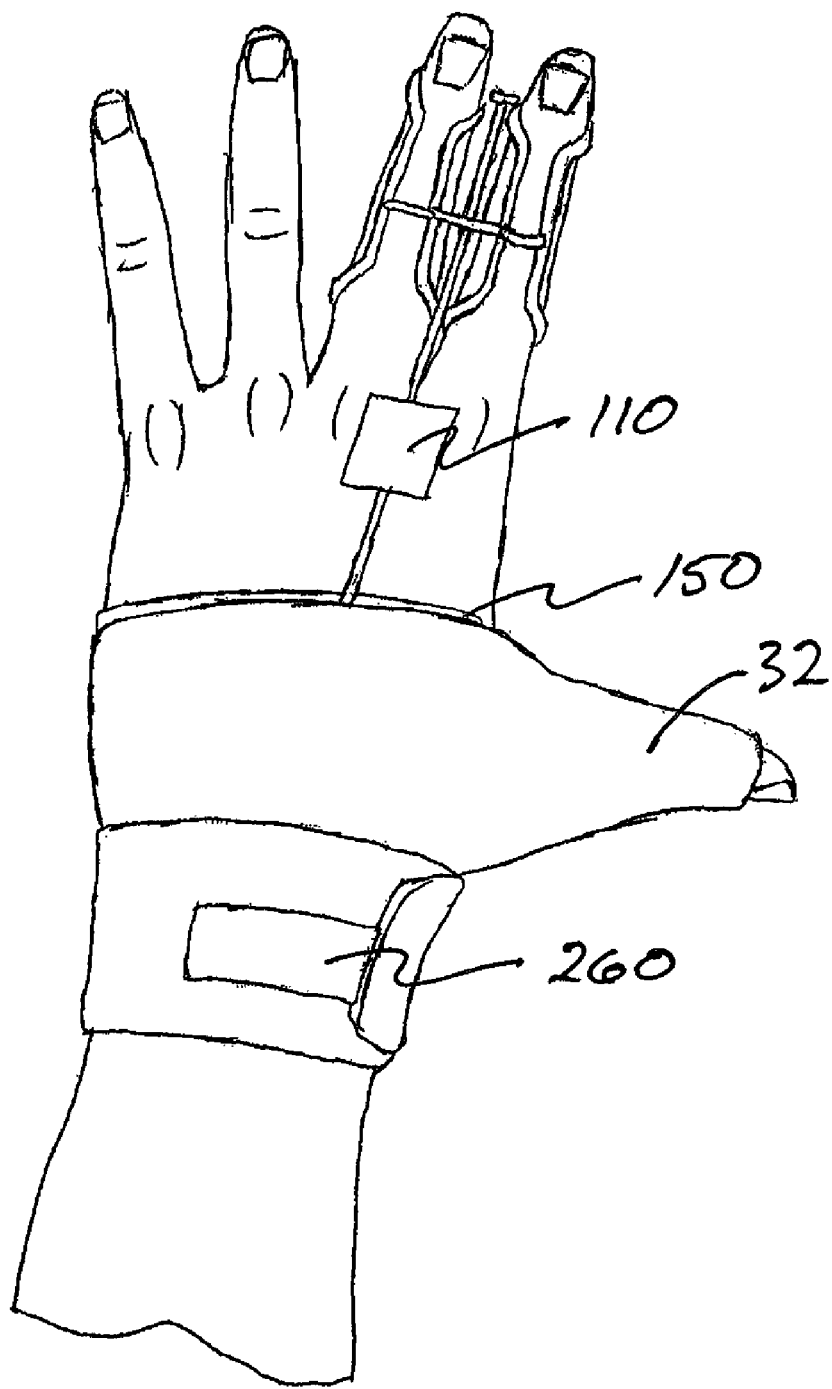
FIG. 16 schematically illustrates a top view of a splint having an alternative configuration of the platform, with the splint mounted on a person's left hand showing the dorsal side of the hand with the handwrap in a closed position.

The extension assembly 100 may be attached to the glove 20 by cooperation between the proximal end of the outrigger rod 91 and the mounting platform 50, FIGS. 2-6. The mounting platform 50 may be secured to the underside 33 of the glove 20 using any suitable fastening mechanism. For example, a fastener 70, which may comprise a hook-and-loop fabric, may optionally be attached to the surface of the platform 50 that contacts the underside 33 of the glove 20 to secure the platform 50 to the glove 20, FIG. 10. The platform 50 may be composed of a semi-rigid resilient material such as a thermoplastic, and may have a soft, resilient platform pad 51 attached to the surface of the platform closest to the individual's hand to provide a cushion between the platform 50 and the dorsum of the individual's hand, FIG. 8. As used herein, the term "semi-rigid" describes a material capable of being bent but able to return to its shape upon release of the bending force. If the platform 50 is made from Aquaplast® plastic, the material may be shaped by first heating the plastic in hot water and manipulating the plastic while it is warm into the desired configuration. The platform's thickness may vary depending on the material used and depending on the desired rigidity. Experimentation with differing platform thicknesses has shown that a thickness of about ⅛ inch is sufficient for a platform made of Aquaplast® plastic. The platform 50 may extend along a portion of the width of the hand as shown in FIG. 15 or may extend the entire width of the hand as shown in FIG. 16. Additionally or alternatively, a platform 50 may extend the length of the glove 20 to provide the individual with additional surface area to distribute pressure forces when needed.

Figure 5:
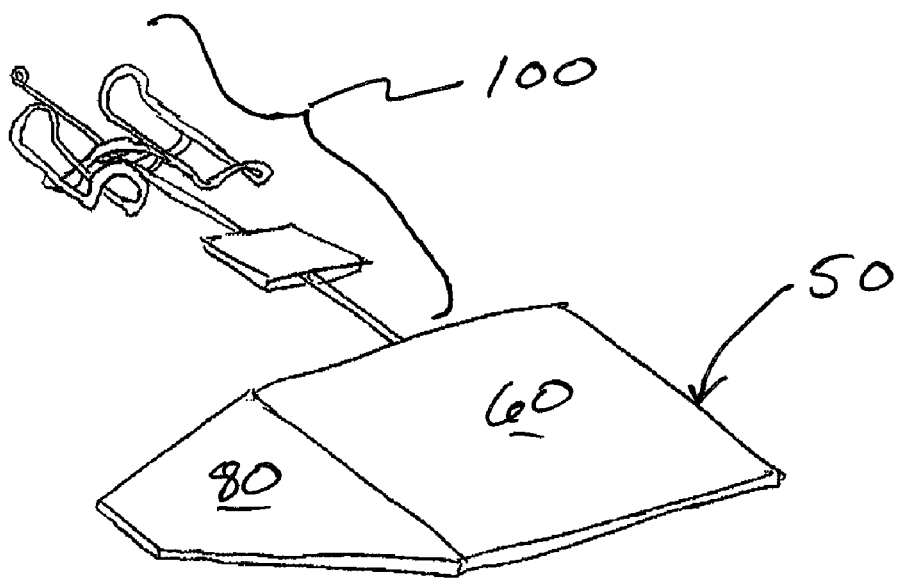
FIG. 5 schematically illustrates a perspective view of the underside of the extension assembly attached to a platform.

The platform 50 provides an outrigger mount portion 60 to which the outrigger 90 may be attached, FIG. 5. In addition, the platform 50 may optionally include a thumb extension portion 80 that slides into the thumb jacket 32 to act as a splint to apply an extension force against the thumb to straighten the thumb. The thumb jacket 32 alone may be sufficiently stiff to bias the individual's thumb to remain extended. In other cases, the thumb extension 80 may be used to complement the glove's natural extension force.

Figure 6:
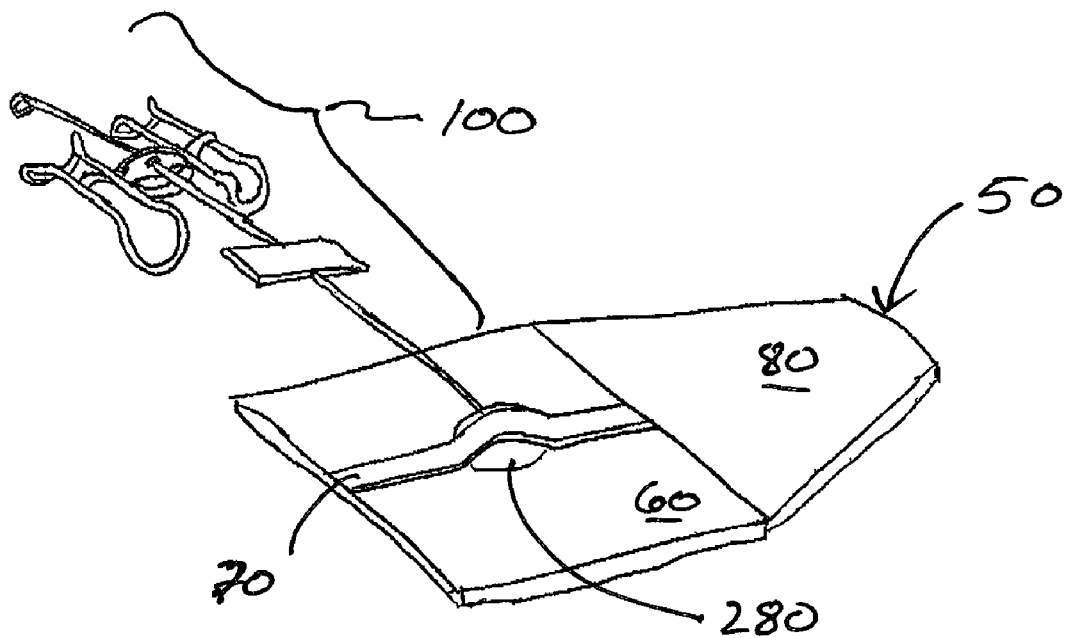
FIG. 6 schematically illustrates a perspective view of the top side of the extension assembly and the platform.
Figure 7:
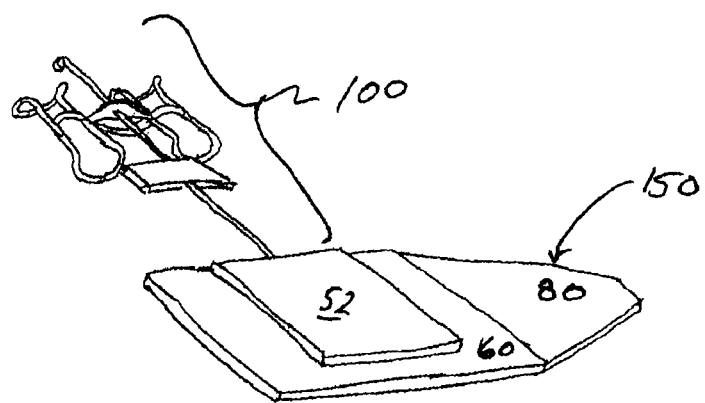
FIG. 7 schematically illustrates a perspective view of the top side of an alternative configuration of an extension assembly and platform.

The outrigger 90 may be attached to the platform 50 via a platform fastening material 280 such as an adhesive or any other suitable material, FIG. 6. In such a configuration, the fastener 70 may be provided over the platform fastening material 280, FIG. 6. Additionally, as shown in FIG. 7, the outrigger 90 may be sandwiched between the platform 50 and a second platform provided in the form of a platform patch 52. The platform patch 52 may be bonded, glued, melted, welded or otherwise fixed to the platform 50. If a thermoplastic patch 52 and platform 50 are used, the two pieces may be heated and melted together to form one thicker platform with the outrigger 90 sandwiched between the platform 50 and platform patch 52.

Figure 17:
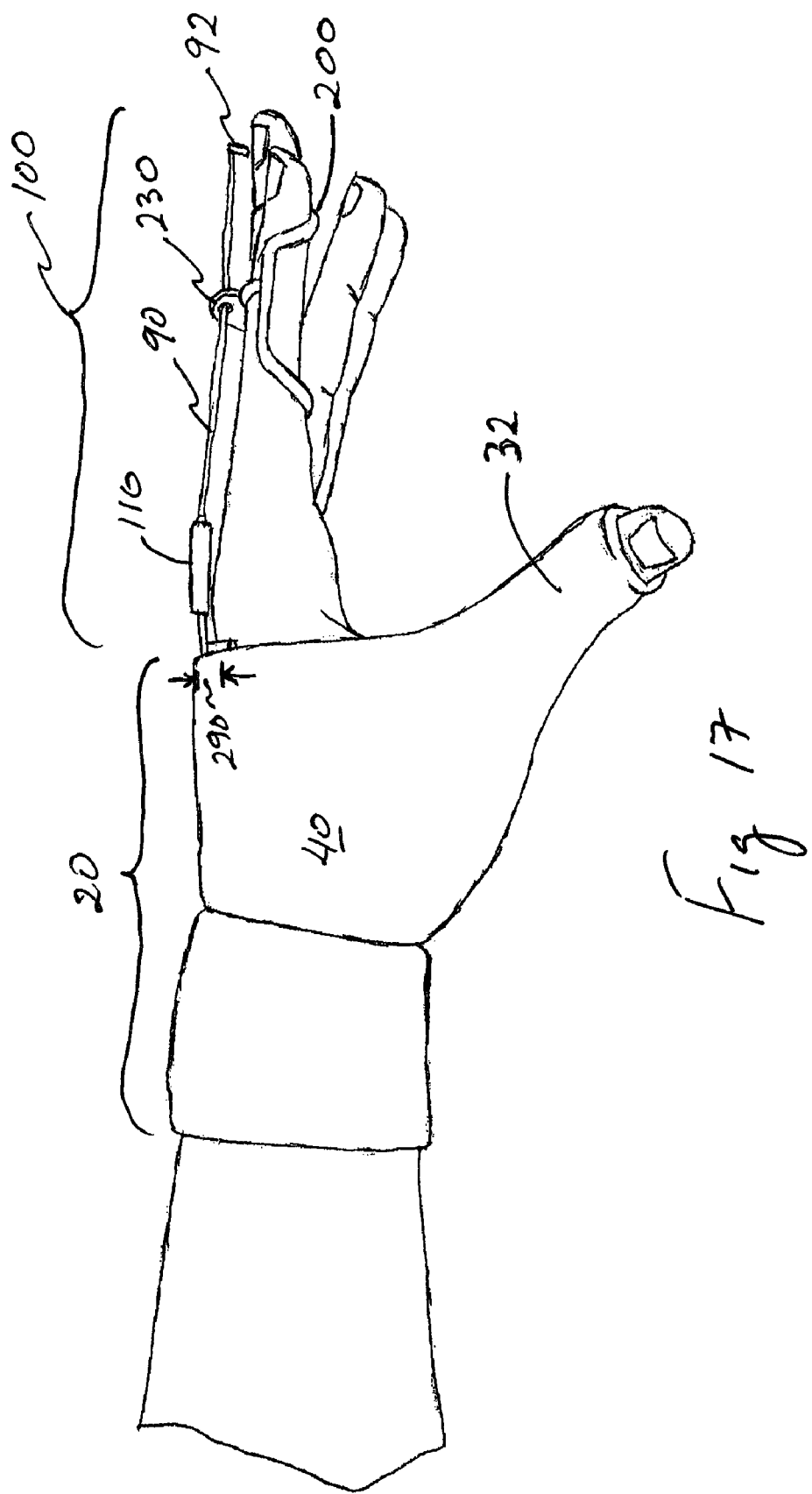
FIG. 17 schematically illustrates a side elevational view of the splint mounted a on person's left hand showing the side of the hand with the fingers extended.
Figure 18:
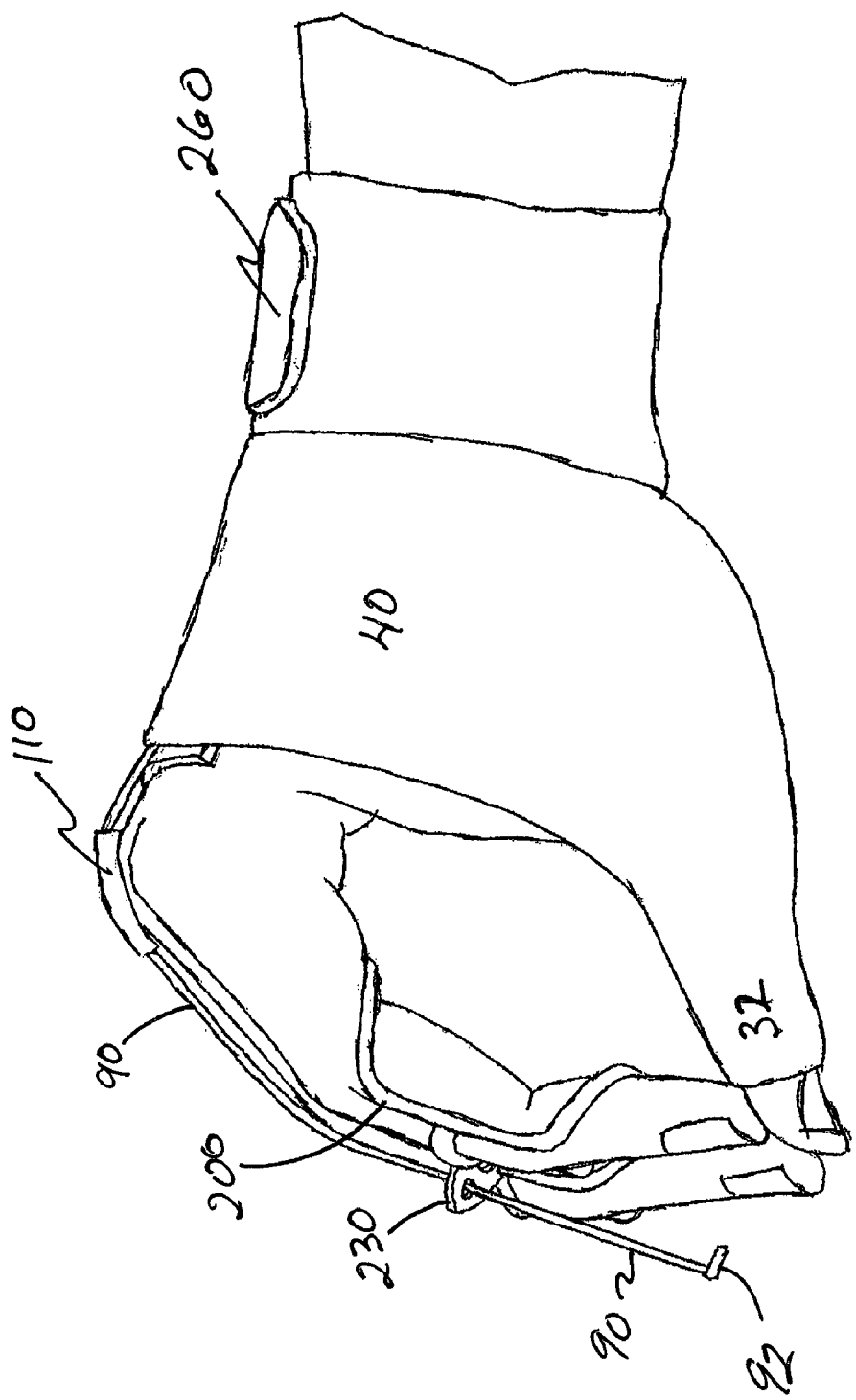
FIG. 18 schematically illustrates a side elevational view of the splint mounted on a person's right hand showing the side of the hand with the index and long finger closed in a tripod grip with the thumb.

The outrigger 90 may extend away from the platform 50 proximate to the plane of the outrigger mount portion 60 to provide the low-profile configuration of the dynamic extension splint 10, FIG. 17. A total profile thickness 290 of less than one inch, as measured from the dorsum of the hand upward to the top of the outrigger 90, provides the wearer with increased dexterity and is less conspicuous to other individuals, FIG. 17. One exemplary configuration of a low-profile splint 10 in accordance with the present invention having a total height profile thickness of less than ½ inch can be achieved using Neoprene® elastomer for the glove 20 and Aquaplast® plastic for the platform 50.

To prevent discomfort caused by the outrigger 90, an optional outrigger cushion pad 110 may be attached to the outrigger 90 using a pad fastening material 250, which may include an adhesive, a tape such as Coban® tape, or any other suitable material. The cushion pad 110 (like the platform pad 51) may be composed of soft materials like sponges, cotton, polystyrene (PS), ethylene-vinyl acetate (EVA), or a Durafoam® pad (a closed-cell sponge composed of rubber and plastic foam).

Figure 12:
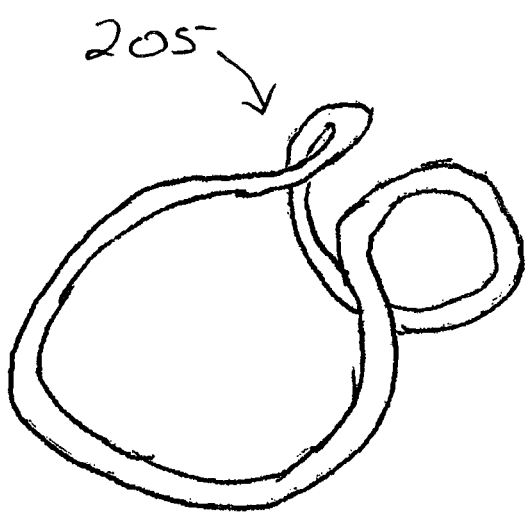
FIG. 12 schematically illustrates a perspective view of an alternative configuration of the finger extender.
Figure 13:
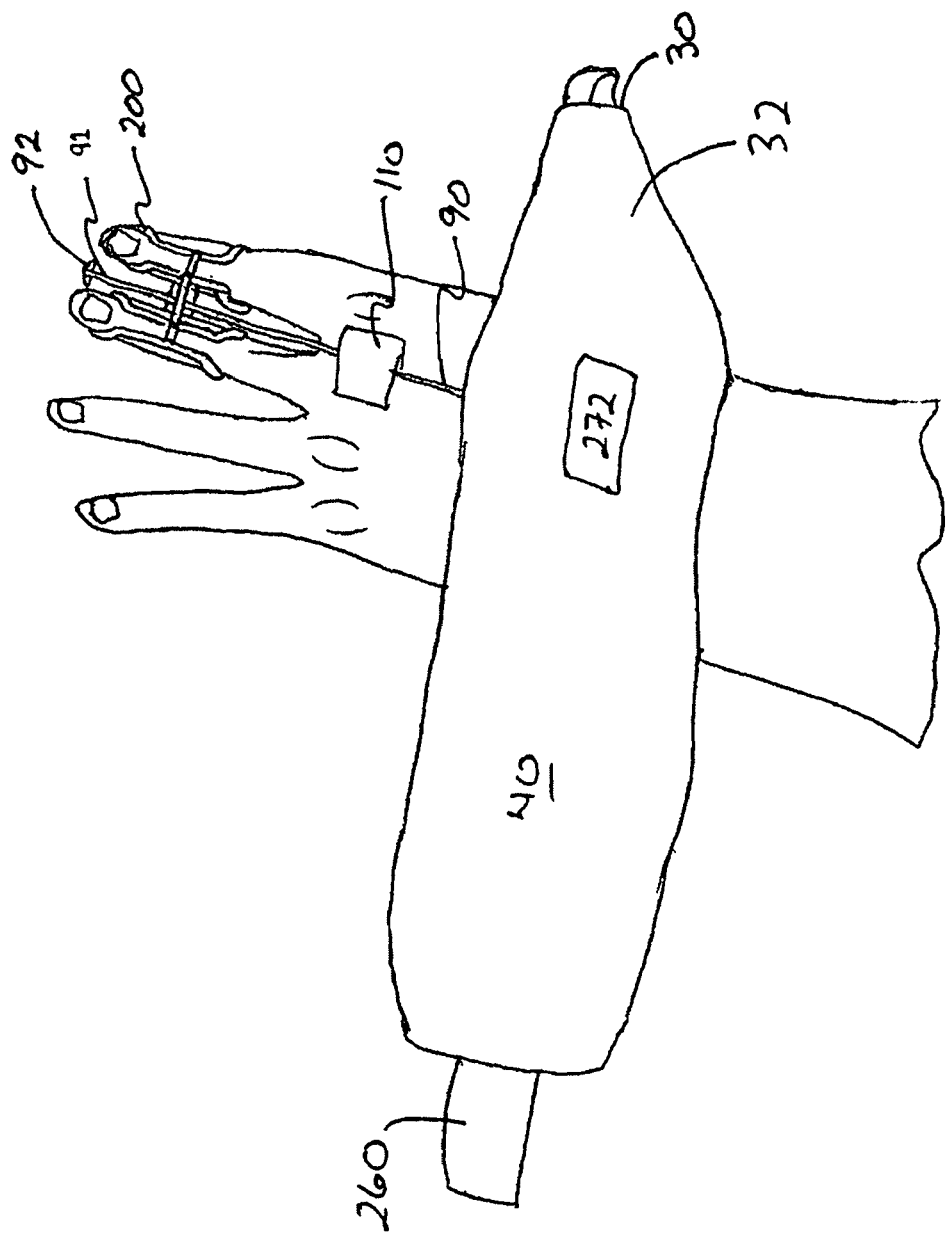
FIG. 13 schematically illustrates a top view of the splint mounted on the person's left hand showing the dorsal side of the hand with the handwrap in an opened position.

To prevent flexion of one or both of the interphalangeal joints and to hold the individual's finger(s) in position relative to the outrigger 90, one or more finger extenders 200 may be attached to the outrigger 90 using a finger extender bridge 230. Attaching two finger extenders 200 on either side of the outrigger 90 provides a buddy-splinting configuration in which two adjacent fingers are secured together. The finger extender(s) 200 may be provided in the form of a finger splint, tube, brace, or an Oval-8 splint (a seamless, molded, plastic splint manufactured by 3 Point Products, Stevensville, Md.) The finger extender 200 may include a cradle or a warped circular saddle 210 supporting the palmar side of the individual's finger(s) and a half ring bridge 220 supporting the dorsal side of the individual's finger(s). Alternatively, the finger extender 205 may be provided without the half ring bridge 220, FIG. 12. The finger extender(s) may be sized to fit snuggly around the individual's fingers.

To attach the finger extender(s) 200 to the outrigger 90, the finger extender bridge 230 may include a hole 231 through which the outrigger 90 may pass. The finger extender bridge 230 may be affixed to the outrigger 90 using materials such as string, adhesive, or thermoplastics such as Aquaplast® plastic (a hard, semi-rigid, resilient plastic made by WFR/Aquaplast Corporation and distributed by Sammons Preston), Aquaflex® plastic (splint casting material made by Roylan), or other suitable materials. For example, in addition to thermoplastics, chemical resins, epoxies, or irradiation plastics may be used. Other examples of suitable thermoplastic materials may include polyacrylates (acrylic), polyoxymethylene, polysulfone (PSU), polycarbonate (PC), and polyvinyl chloride (PVC). The finger extender(s) 200 may be slidably attached to the outrigger 90 to permit the finger extender(s) 200 to move along the outrigger 90 when the outrigger bends 90. In this regard, the outrigger 90 may be slid through the hole 231 in the finger extender bridge 230. To help prevent the finger extender(s) 200 from sliding off the distal end of the outrigger 90, a plastic or rubber stop 92 may be added to the distal tip of the outrigger 90. In addition for configurations of the dynamic extension splint 10 that have a plurality of finger extenders 200, it may be desirable to fix the finger extenders 200 together via a fastening material to improve their mechanical rigidity, such as Coban® tape (an elastic, self-adhesive tape made by Nexcare and 3M), a thermoplastic, or other fastening material.

Figure 14:
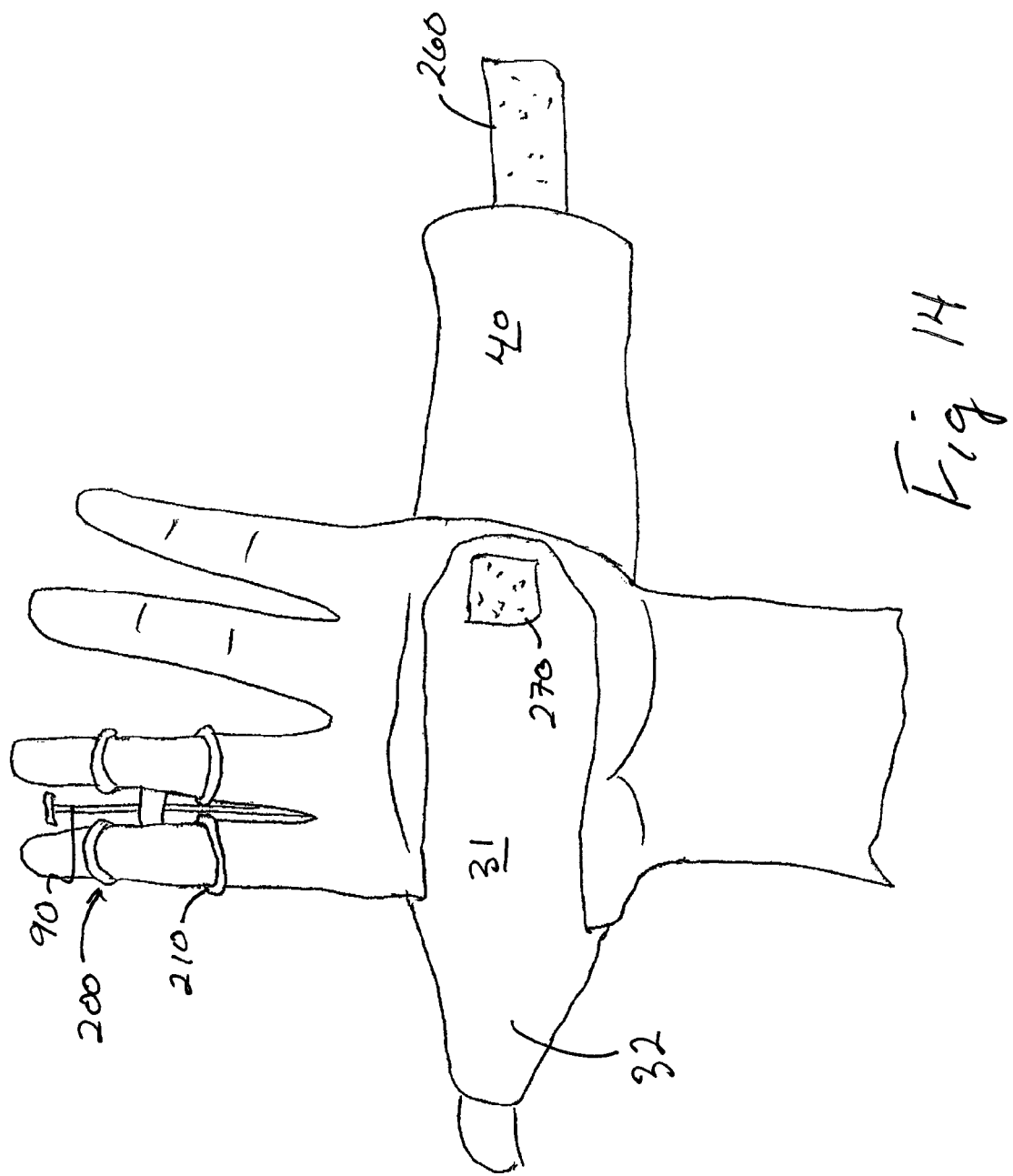
FIG. 14 schematically illustrates a bottom view of the splint mounted on the person's left hand showing the palmar side of the hand with the handwrap in an opened position.

In use, when donning the dynamic extension splint 10, the individual opens the glove 20 by moving the thumb opening flap 31 away from the handwrap 40 (open position, FIG. 3) and sliding his or her thumb into the thumb jacket 32 and through the thumb opening 30, thereby placing the dorsum of the hand into contact with platform 50. Additionally, the individual slides one or more fingers into the finger extender(s) 200 which are connected to the platform via flexible outrigger 90 to prevent flexion along one or more of the interphalangeal joints, FIGS. 13-18. As shown in FIGS. 13-18, the two finger extenders 200 prevent flexion along both the DIP (distal interphalangeal) and PIP (proximal interphalangeal) joints. The individual may then wrap the handwrap 40 around his or her hand and/or wrist and attach an optional hook-and-loop strap 260 to an optional hook-and-loop pad 272. Depending on the configuration, the handwrap 40 can be wrapped two or more times around the individual's wrist, or the glove can be secured by other fastening mechanisms such as Velcro™ fasteners, strings, buttons, zippers, etc. As shown in FIG. 14, when a left-handed glove is worn with the palm facing upwards, the outrigger 90 will be positioned to the right of the individual's left index finger and to the left of the individual's long finger. When the individual flexes his or her finger(s) the outrigger 90 is curved into an arcuate shape increasing the potential energy of the outrigger, FIG. 18. The outrigger 90 applies a force against the user's fingers through the finger extender(s) 200. Without the aid of the splint 10, the affected individual's fingers and thumb would be partially or completely curled closed (flexed). While wearing the splint, the individuals fingers and thumb remain at least partially open (extended), as would normally be the case for an individual not suffering from flexor spasticity, FIGS. 17-18. When the individual flexes the muscles in his or her hand and grasps an object, the outrigger 90 applies a biasing force against the flexion of the individual's finger(s). The biasing force transmitted to the finger(s) through the finger extender(s) 200 and outrigger 90 allows the individual's fingers to return to an extended position once flexion forces are sufficiently diminished.

In the configuration shown in FIGS. 1-4, the rod 91 causes the biasing force against the individual's fingers, which is advantageous over parts like rubber bands, wires, and springs that tend to wear out and break requiring replacement parts. Additionally, using the rod 91 as a source of the biasing force allows for configurations of the dynamic extension splint 10 to be optionally composed of essentially four components: the glove 20, the platform 50, the outrigger 90, and a finger extender 200. Other configurations having added features may contain additional parts such as: two finger extenders 200, a platform pad 51, an outrigger pad 110, or an thumb extension portion 80. To adjust the biasing force of the outrigger 90, the thickness of the outrigger 90 can be modified, or the composition of the outrigger changed 90. Alternatively, optional outrigger tension adjustment mechanisms 300, 400 may be provided to permit adjustment of the tension or biasing force provided by the outrigger, FIGS. 19-21.

Figure 19:
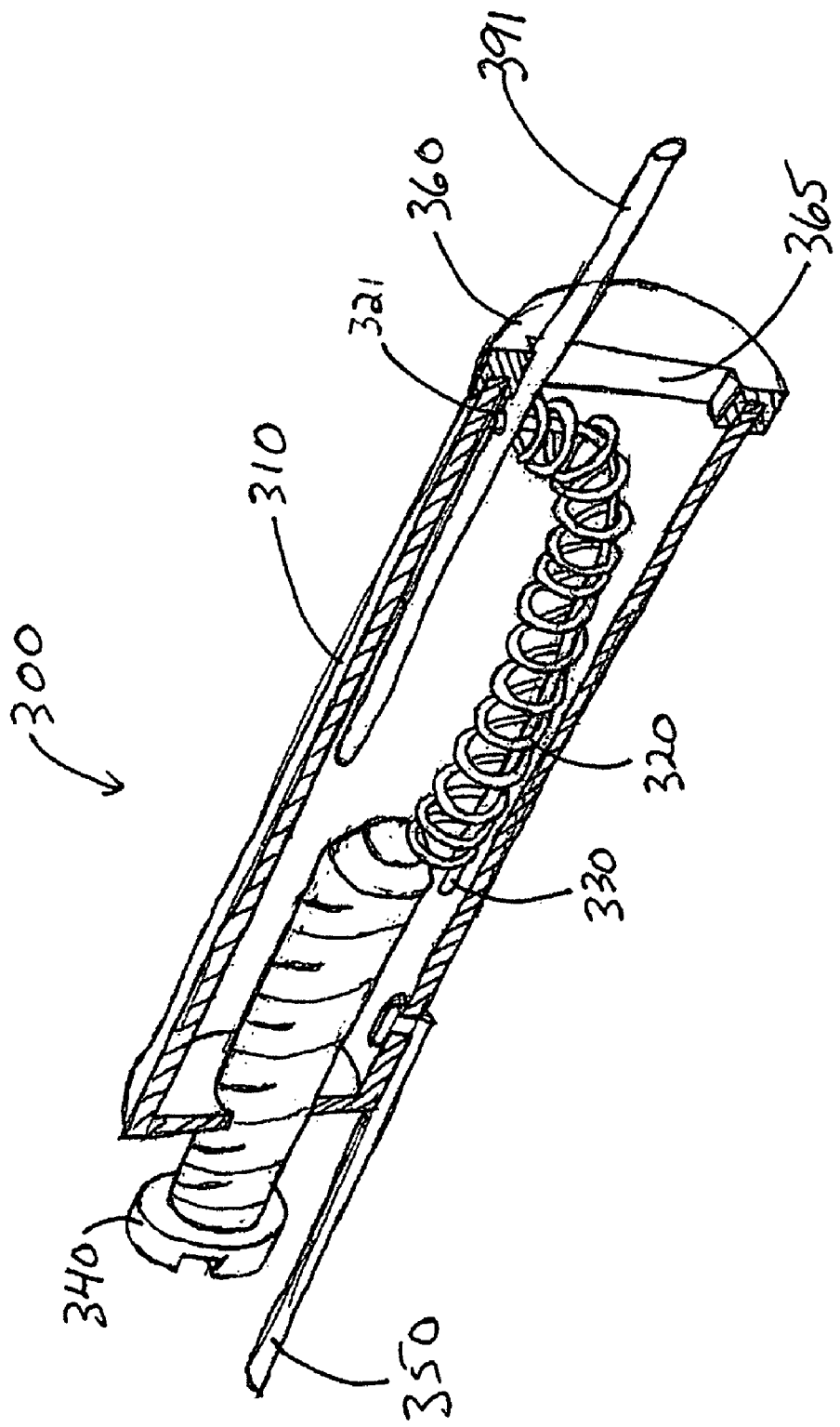
FIG. 19 schematically illustrates a cross-sectional perspective view of an outrigger tension adjustment mechanism.
Figure 20:
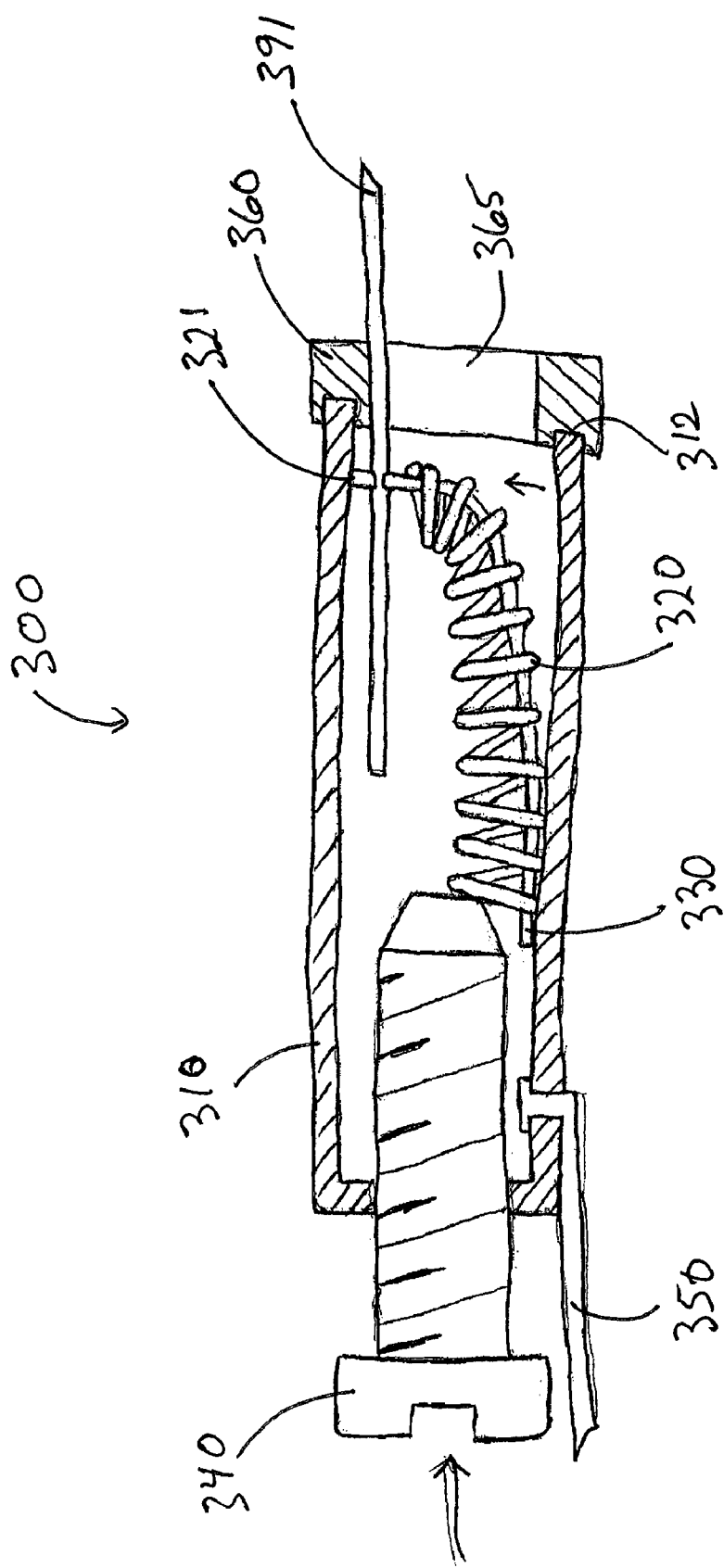
FIG. 20 schematically illustrates a cross-sectional side elevational view of the outrigger tension adjustment mechanism of FIG. 19.

For example, FIGS. 19 and 20 schematically illustrate cross-sectional perspective and side elevational views, respectively, of one exemplary configuration of an outrigger tension adjustment mechanism 300 in accordance with the present invention. The outrigger tension adjustment mechanism 300 may include a housing 310 that may have a generally cylindrical shape. The housing 310 may be attached to the mounting platform 50 of the glove 20 by securing a mounting arm 350 to the mounting platform 50 by any suitable method. For example, the mounting arm 350 may be attached to the mounting platform 50 by any of the methods described above for attaching the outrigger rod 91 to the mounting platform 50. An L-shaped guide wire 330 may be provided internally to the housing 310 having a distal end 321 that extends upward towards the top of the housing 310. An outrigger rod 391 is provided having a hole through which the distal end 321 of the guide wire 330 extends so that the outrigger rod 391 may be slidably disposed on the guide wire 330. Thus, when the outrigger tension adjustment mechanism 300 is optionally included on a splint of the present invention, the outrigger rod 391 is not directly attached to the mounting platform 50. Rather, the outrigger tension adjustment mechanism 300 may be attached to the mounting platform 50 by the mounting arm 350, and the outrigger rod 391 may be attached to the opposing distal end of the housing 310.

A vertically oriented slit 365 is provided at the end of the housing 310 distal to the mounting arm 350 through which the outrigger rod 391 extends to permit the outrigger rod 391 to travel vertically in the slit 365. The slit 365 may be provided as part of the distal housing end 312 or may be provided as part of a cap 360 fitted onto the distal end 312 of the housing 310. To regulate the range of vertical motion of the outrigger rod 391, and thus the biasing force provided by the outrigger rod 391, a coil spring 320 is provided within the housing 310 and is wound around (or slid over) the guide wire 330. A tension adjustment screw 340 is provided at the end of the housing 310 proximate the mounting arm 350, with the shaft of the screw 340 extending internally to the housing 310. The internal end of the screw 340 contacts the end of the spring 320 furthest from the outrigger rod 391. As the screw 340 is rotated into the housing 310, the spring 320 is compressed and rides along the guide wire 330 to provide an upward directed force to bias the outrigger rod 391 towards the top of the housing 310, FIG. 20. As the screw 340 is rotated further into the housing 310 the upward force provided by the spring 320 on the outrigger rod 391 is increased, which in turn decreases the ability of the outrigger rod 391 to travel in the downward direction within the slit 365, resulting in an outrigger rod 391 with less mobility, and therefore, an outrigger rod 391 that provides a greater extension force against the fingers of the individual.

Figure 21:
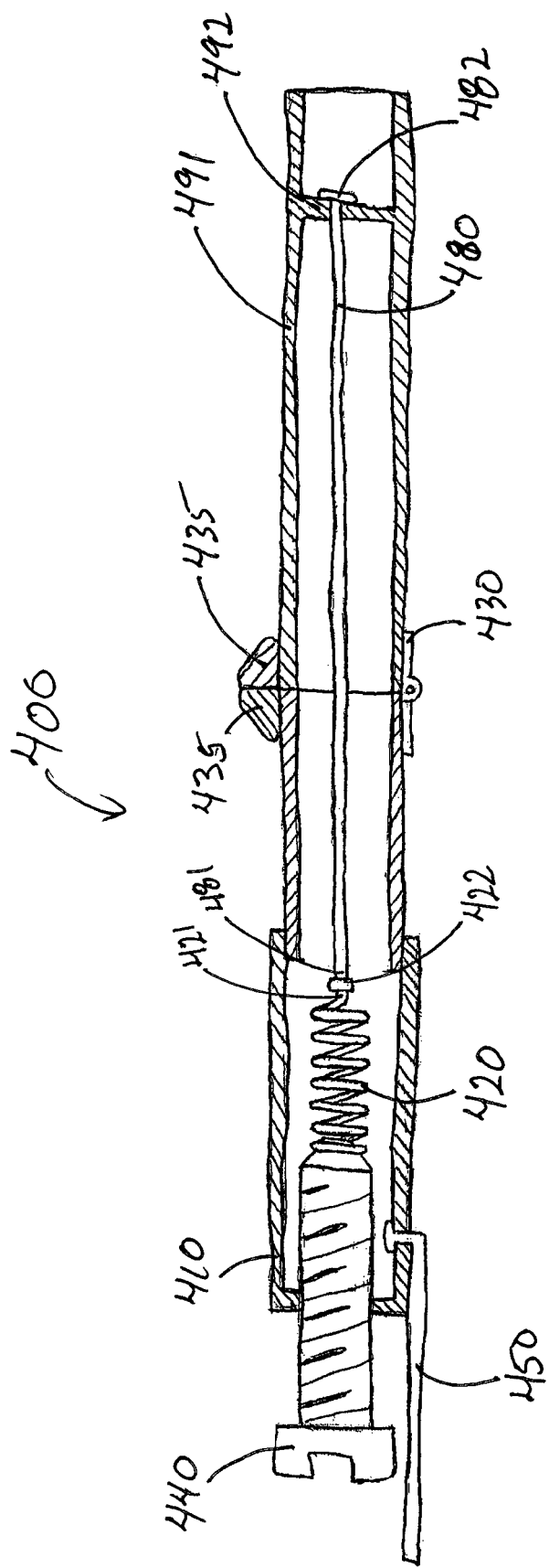
FIG. 21 schematically illustrates a cross-sectional side elevational view of another outrigger tension adjustment mechanism.

Turning to FIG. 21, an additional exemplary configuration of a tension adjustment mechanism 400 in accordance with the present invention is illustrated in cross-sectional side elevational view. The outrigger tension adjustment mechanism 400 may include a housing 410 that may have a generally cylindrical shape. The housing 410 may be attached to the mounting platform 50 of the glove 20 by securing a mounting arm 450 to the mounting platform 50 by the methods described above with regard to the tension adjustment mechanism 300. An outrigger rod 491 may be attached to the end of the housing 410 distal to the mounting arm 450. The outrigger rod 491 may optionally be provided in two portions joined together by a hinge 430 to allow the outrigger rod 491 to bend at the hinge 430 in the downward direction towards the individual's palm. The hinge 430 may be provided along the length of the outrigger rod 491 at a location that would position the hinge 430 over one of the interphalangeal joints. To assist in preventing hyperextension, a pair of hyperextension stops 435 may be provided on the upper surface of the outrigger rod 491 opposing the hinge 430.

To adjust the ease with which the outrigger rod 491 may be bent, a tension wire 480 may be provided along the outrigger rod 491 along with a coil spring 420 and tension adjustment screw 440 in the housing 410. The tension wire 480 may be provided internally to a hollow outrigger rod 491 and secured in place via a stop 482 on the end of the tension wire 480 that abuts an internal wall 492 of the hollow outrigger rod 491. Alternatively, the tension wire 480 may be provided externally to, and run along the exterior of, the outrigger rod 492, with the end of the tension wire 480 furthest from the housing 410 secured to the outrigger rod 492 by a screw or other suitable fastening mechanism. In such an alternative configuration, the outrigger rod 492 need not be hollow.

The distal end 421 of the coil spring 420 may be attached to the proximal end 481 of the tension wire 480 by a crimped metal sleeve 422 or other suitable attachment mechanism. The tension adjustment screw 440 may be provided at the end of the housing 410 proximate the mounting arm 450, with the shaft of the screw 440 extending internally to the housing 410. The internal end of the screw 440 may be attached to the end of the spring 420 furthest from the outrigger rod 491. As the screw 440 is rotated into the housing 410, the spring 420 is compressed and foreshortened to decrease the force with which the spring 420 pulls on the tension wire 480. As a screw 440 is rotated further into the housing 410 the pulling force provided by the spring 420 on the tension wire 480 is decreased, which in turn increases the ability of the outrigger rod 491 to bend downwards, resulting in an outrigger rod 491 with increased mobility, and therefore, an outrigger rod 491 that provides a decreased extension force against the fingers of the individual.

Various methods of making and assembling the components of the functional local profile dynamic extension splint 10 of the present invention are also provided including various methods for selecting appropriate parts for the splint 10, and for properly fitting the splint 10 to an individual's hand. Specifically, the methods include steps for: A.) manufacturing the platform 50; B.) determining the size of the thumb jacket 32; C.) manufacturing the optional thumb extension portion 80 of the platform 50; D.) attaching two finger extenders 200 together to form a buddy splint; E.) attaching the finger extender bridge 230 to the finger extender(s) 200; F.) attaching the finger extender(s) 200 to the outrigger 90; G.) selecting a rod 91 having the appropriate rigidity for use in the dynamic extension splint 10; and, H.) attaching a rod 91 having the appropriate rigidity to the platform 50.

A.) To manufacture the platform 50 for the functional low-profile dynamic extension splint 10, draw an outline of the dorsum of the affected hand on a piece of paper or other writing surface. Along the dorsum of the hand, ¼ inch proximal to the knuckle of the index finger, draw a line vertically along the mid-radial border of the second metacarpal to ½ inch proximal to the carpometacarpal (CMC) joint. Draw another vertical line from ¼ inch proximal to the knuckle of the small finger to ½ inch distal to the CMC of the 5th metacarpal. Draw a horizontal line on the paper connecting the top of the vertical line ¼ inch below the knuckle of the index finger to the top of the vertical line ¼ inch below the small finger. Draw a horizontal line at the bottom mark ½ inch distal to the CMC of the index finger to the bottom of the line ½ an inch distal to the CMC of the small finger. Cut out the drawing using a scissor or other cutting tool. Trace the drawing using a wax marking pencil or other drawing tool onto a thermoplastic slab. Use a shears or cutting tool to cut out the drawing traced on the thermoplastic slab. Heat the slab in a water tray until the slab becomes transparent; allow the slab to cool to a temperature where the slab will not be able to cause damage to the skin, but will be still playable to mold to the dorsum of the hand, and allow the slab to cool and harden into the platform 50. If constructing a dynamic extension splint with a platform pad 51, the method of making the platform may include the following steps. Place the thermoplastic cutout onto the surface of the platform pad. Use a drawing tool to trace the outline of the cutout onto the pad. Cut out the outline traced onto the pad, and secure the pad to the palmar surface of the slab. FIGS. 4, 5, 7, 8, and 10 illustrate various configurations of the platform 50 that can be made by this method.

Figure 2:
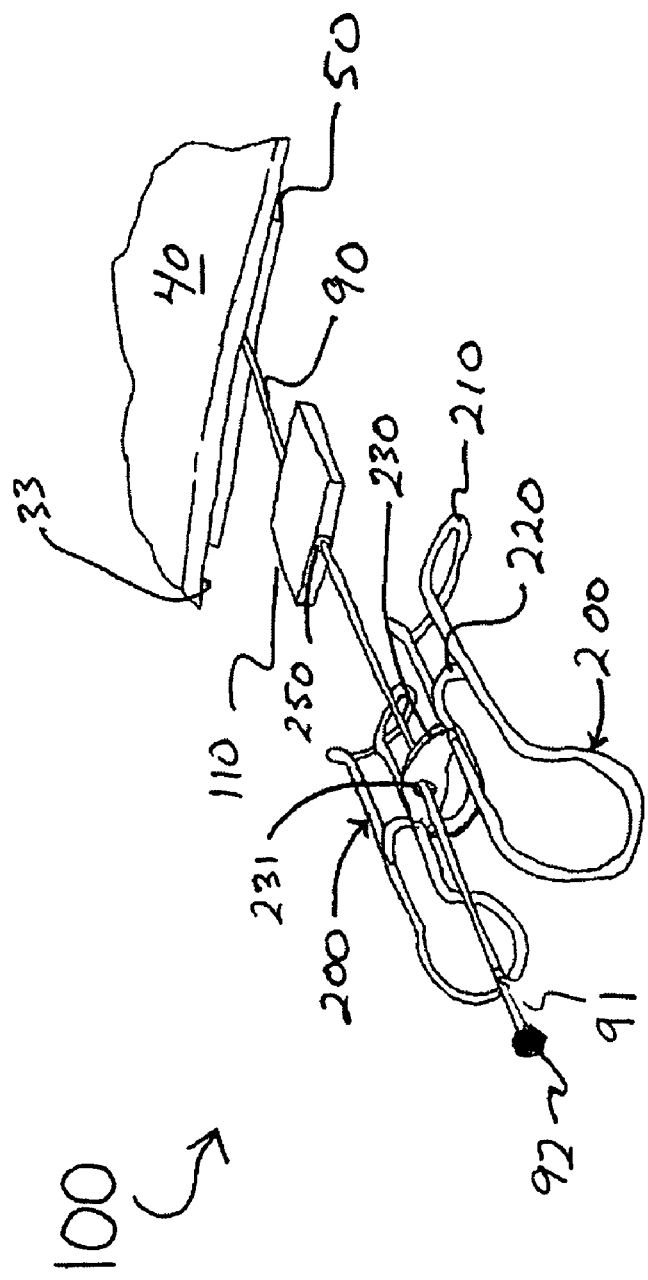
FIG. 2 schematically illustrates a perspective fragmentary view of the splint of FIG. 1 illustrating the extension assembly.
Figure 3:
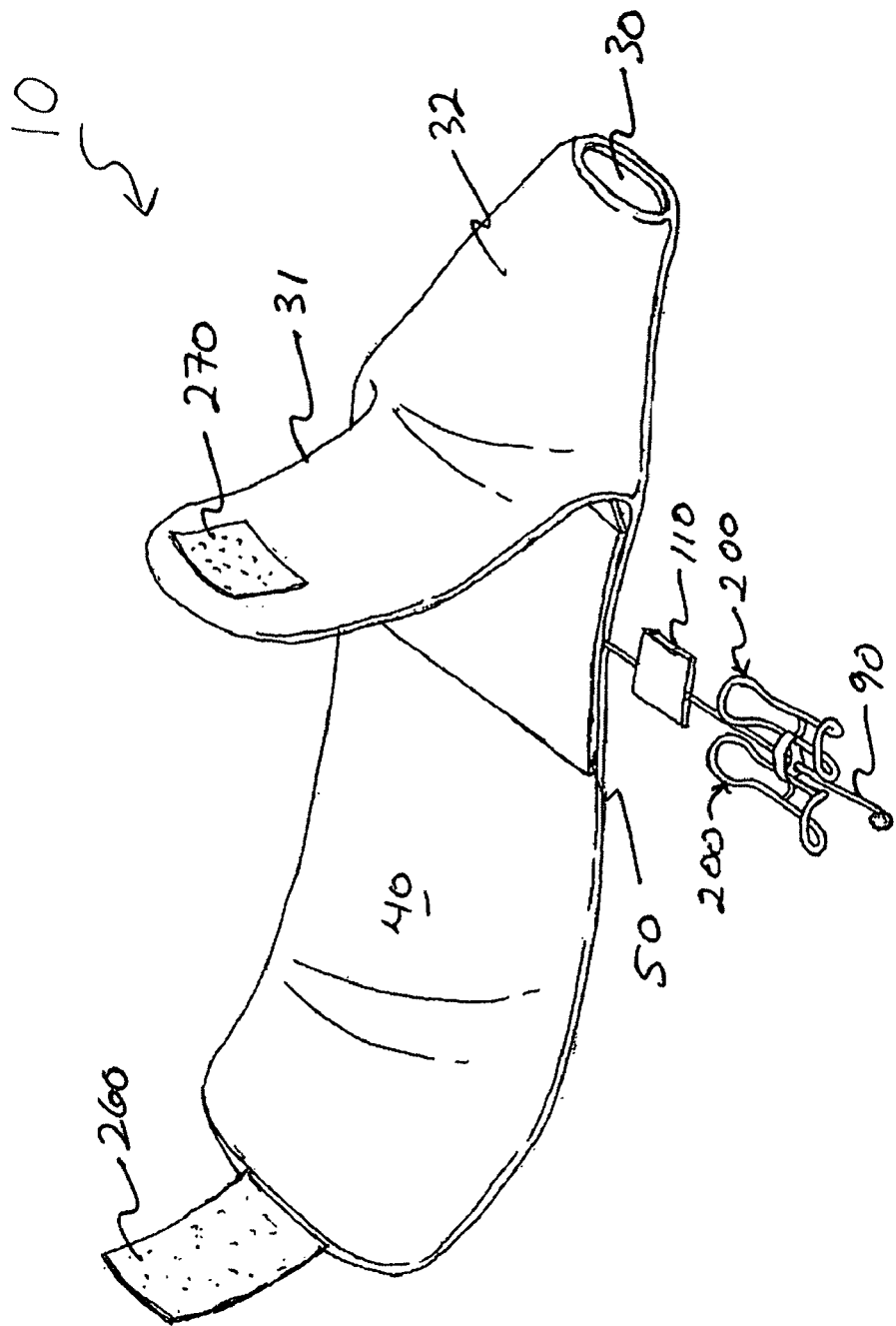
FIG. 3 schematically illustrates a perspective view of the splint of FIG. 1 showing the underside of the splint.
Figure 4:
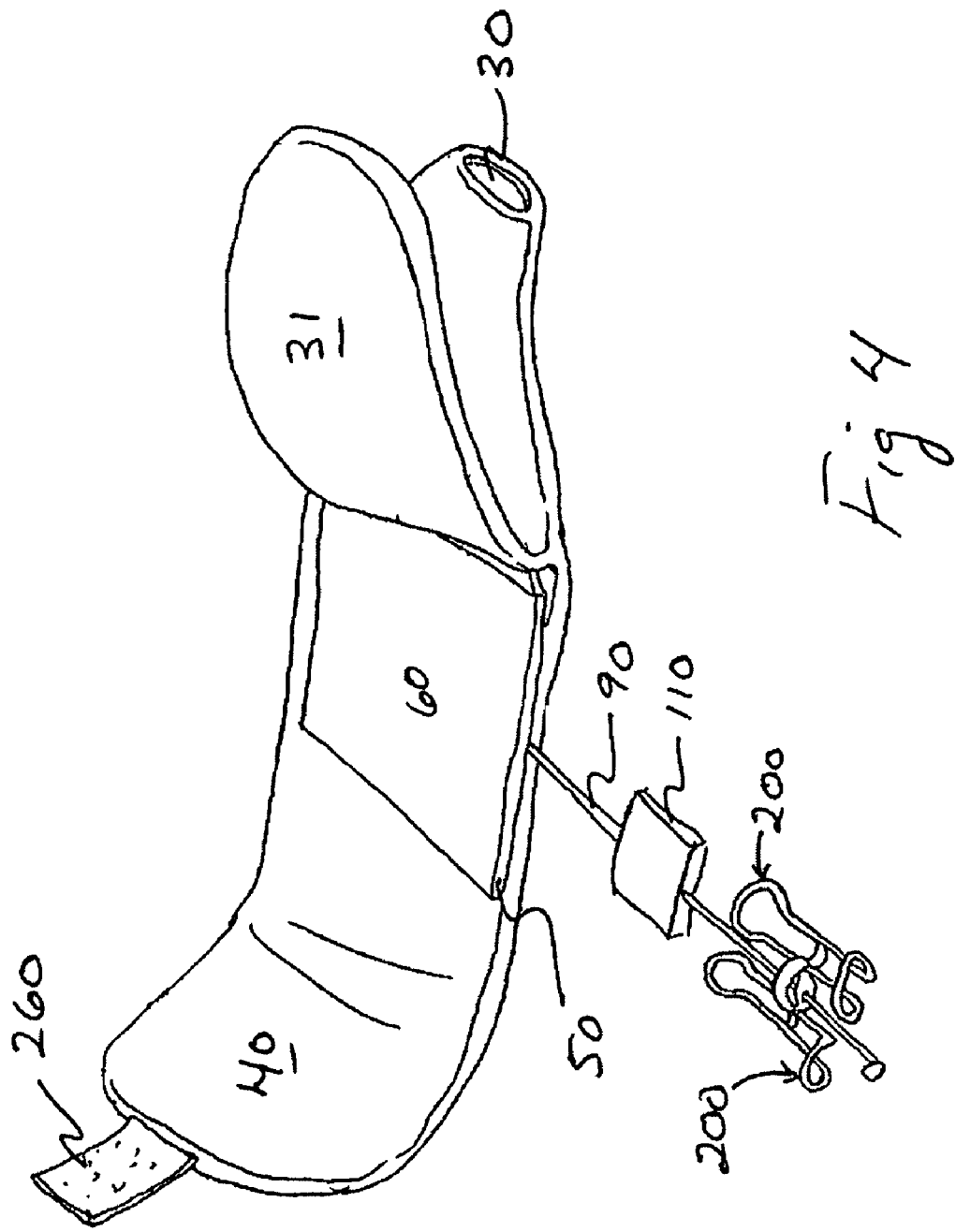
FIG. 4 schematically illustrates a perspective view of the splint of FIG. 1 showing the underside of the splint with the thumb flap placed in an open position.

B.) To determine the size and length of the thumb jacket 32, begin by positioning the platform 50 on top of the dorsum of the affected hand. Place the glove 20 over the platform 50 and around the hand. Secure the thumb opening 30 around the thumb. Inspect the thumb opening 30 to make sure the distal portion of the thumb opening 30 rests between the IP joint and the thumb tip to block the thumb from over flexing at the IP joint when attempting to make a tripod pinch with the spastic hand. Trim the thumb jacket 32 down to terminate at the point between the PIP joint and thumb tip, if the thumb jacket 32 is too long. FIGS. 2-4 illustrate an example of a thumb jacket 32 made by this method.

Figure 10:
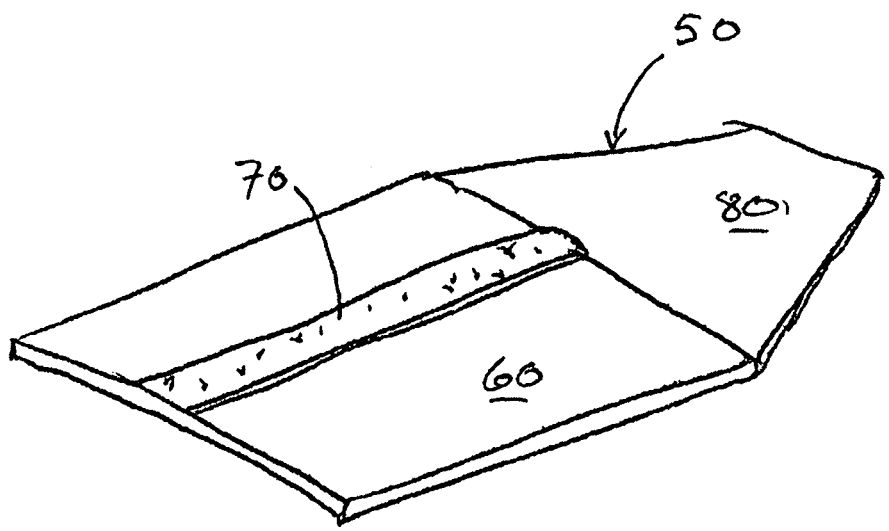
FIG. 10 schematically illustrates a perspective view of the platform.
Figure 11:
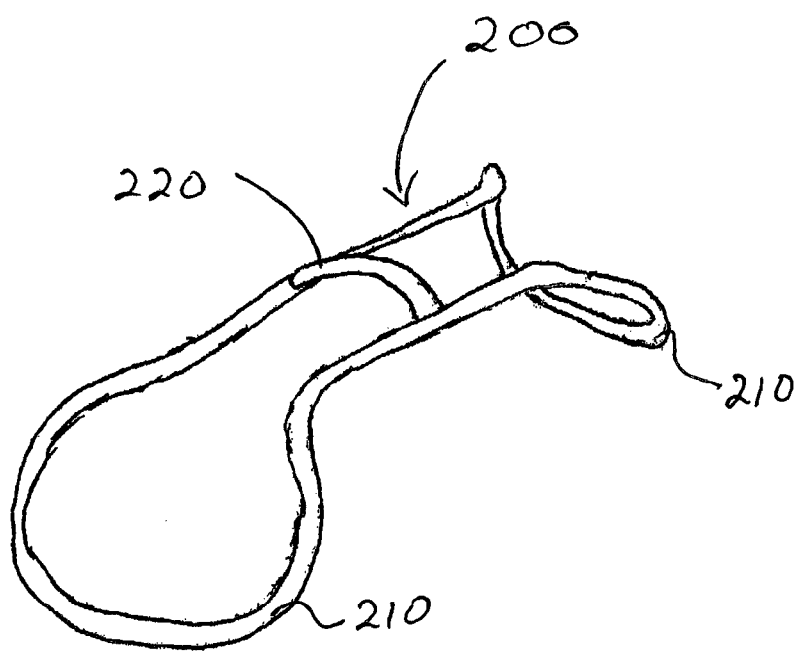
FIG. 11 schematically illustrates a perspective view of a finger extender.

C.) For certain individuals, the thumb may have residual spasticity even with the thumb jacket 32 equipped. Consequentially, the thumb may abduct past the index and long finger when the individual attempts to close his or her hand. To assist this type of individual, a thumb extension portion 80 of the platform 50 may be used to provide a cooperative extension force with the thumb jacket 32 against the person's thumb. To manufacture and attach the optional thumb extension portion 80 of the platform 50, begin by providing an outrigger mount portion 60 of the platform 50 and a slab. The outrigger mount portion 60 and slab may comprise thermoplastics other appropriate materials, such as Aquaplast® plastic, for example. Hold the outrigger mount portion 60 in place on the dorsum of the affected hand. Measure the distance from the web space of the hand to the IP joint of the thumb. Draw a rectangle or oval shaped pattern with a writing tool on the slab, so that the pattern is approximately two inches wide and approximately two inches longer than the distance from the web space to the IP joint of the thumb. Cut out the pattern on the slab with a shears or other cutting tool to form a thumb extension portion 80 of the platform 50 from the slab. Warm the thumb extension portion 80 and warm the dorsum of the outrigger mount portion 60 using a warming pan, splint gun, or other heating tool. Secure the thumb extension portion 80 to the warmed area of the outrigger mount portion 60 to provide the platform 50 and allow the platform 50 to cool. FIG. 10 illustrates a configuration of a platform made by this process.

D.) To attach two finger extenders 200 together to form a buddy splint, begin by providing a finger extender 200 sized to block the proximal fold of the PIP joint of the index finger to midway between the distal crease of the DIP joint and the finger tip. Provide a second finger extender 200 sized to block the proximal fold of the PIP joint of the long finger to midway between the distal crease of the DIP and the finger tip. Secure the two extenders 200 together with a fastener such as Coban® tape, a plastic tie, or adhesive. The finger extenders 200 may comprise 3 Points Product's Oval-8® splint, or other generic finger extenders 200.

E.) To attach the finger extender bridge 230 to the finger extender(s) 200, begin by heating a thermoplastic strip and then wrap the heated strip around a part of the finger extender 200 to form the finger extender bridge 230. Pinch the sides of the finger extender bridge 230 to flatten the sides of the bridge 230. Form a hole 231 for the rod 91 to slide through in the middle of the flattened finger extender bridge 230. Other materials such as wax, resin, fiberglass, plastic, and polymers can be substituted for the thermoplastic strip as appropriate.

F.) To attach the finger extender(s) 200 to the outrigger 90, begin by inserting an individual's finger(s) into a finger extender(s) 200 and insert the individual's thumb into the thumb opening 30 of the glove 20. Position the platform 50 with attached rod 91 over the dorsum of the hand. Slide the rod 91 through the hole 231 in the finger extender bridge 230 and optionally mount a stop 92 at the distal end of the rod.

G.) To select a rod 91 having the appropriate rigidity for use in the dynamic extension splint 10, begin by positioning the proximal end of the rod 91 on top of the platform 50 so that a portion of the rod 91 is resting on the surface of the platform 50 and the rod 91 is positioned between the metacarpals of two fingers. Place the glove 20 onto the individual's affected hand thereby covering the platform 50 with the glove 20. Insert the individual's fingers into the finger extender(s) 200. Use a second hand to secure the rod 91 to the platform 50 and have the individual close and open the affected finger(s), and observe whether the individual's finger(s) open within about ten degrees or less of full extension. If the fingers do not open within about ten degrees or less of full extension, then replace the rod with a more rigid rod and repeat the previous steps. If the individual is not able to fully flex his or her fingers, then replace the rod with a less rigid rod and repeat the previous steps. In some cases, it may be easier to attach the rod 91 to the platform if the platform is marked with a line. In these cases, the following step may be included: draw a line with a wax pencil or other appropriate marking tool on the platform 50, with the line drawn from the respective location of the MCP joint to the point where the rod 91 will be secured on the platform 50. FIG. 2 illustrates a configuration of a rod made by this process.

H.) To attach the rod 91 having the appropriate rigidity to the platform 50, begin by providing a thermoplastic slab for attaching the rod 91 to the platform 50. Heat the thermoplastic slab with a splint pan or other heating element. Use a splint hot gun or other heating tool to warm the section of the platform 50 predetermined to be attached to the rod 91. Place the proximal end of the outrigger rod along heated section. If a line was made on the platform, align the rod with the previously drawn line, place the heated thermoplastic slab over the rod 91 and attach it to the platform 50, and allow the platform 50 and thermoplastic slab to cool. If a dynamic extension splint with the optional fastener is being constructed, the additional step of placing the fastener on the palmar side of the platform-thermoplastic slab complex may be performed. Once the rod 91 is attached to the platform 50, the platform 50 may be inserted inside the glove 20. If a Neoprene® glove 20 is used and the fastener 70 is a hook-and-loop fastener, the platform 50 may be secured to the Neoprene® by hooking the fastener to the underside 33 of the palmar side of the glove 20.

The above methods can be used to construct splints comprising other materials. For example, materials other than thermoplastic may be used for the platform, such as epoxies, resins, or metals. Further, in most cases several methods exist for constructing each configuration of the splint. For example, in the method above one could substitute the step of tracing the outline of the thermoplastic slab, by attaching a picture of the thermoplastic slab onto the platform pad 51.

Various alternative configurations and modifications to the methods and apparatuses may be made. Many of the methods presented contain optional steps that may be omitted or modified. In addition to the splints depicted and described in the specification, splints designed to extend all four fingers may be used as well as splints having multiple outriggers. It should therefore be understood that this invention is not limited to the particular embodiments described herein, but is intended to include all changes and modifications that are within the scope and spirit of the invention as set forth in the claims.

What is claimed is:

1. A dynamic extension splint for biasing a person's fingers in an open position and having a low-profile configuration, comprising:
    a) a glove designed to wrap around and cover at least a portion of the person's hand including;
        i) a thumb jacket for positioning the person's thumb by covering and securing a portion of the thumb, and
        ii) a handwrap for securing the glove to the person's hand;
    b) a platform for attachment to the glove and configured to rest on the dorsum of the hand, the platform having an outrigger mount portion;
    c) a flexible outrigger for biasing at least two adjacent fingers in an extended open position and attached at a proximal end to the outrigger mount portion of the platform at a location so that the outrigger is positioned between the two adjacent fingers when the splint is being worn, the outrigger including a rod extending away from the outrigger mount portion parallel and proximate to the plane of the outrigger mount portion to provide the low-profile configuration of the dynamic extension splint;
    d) a first finger extender contoured to surround the person's finger including:
        i) a warped circular saddle for supporting the palmar side of the finger, and
        ii) a half ring bridge for supporting the dorsal side of the finger; and
    e) a second finger extender contoured to surround the person's finger including:
        i) a warped circular saddle for supporting the palmar side of the finger, and
        ii) a half ring bridge for supporting the dorsal side of the finger.

2. The dynamic extension splint according to claim 1, wherein the dynamic extension splint comprises a total height profile thickness of less than one inch.

3. The dynamic extension splint according to claim 1, comprising a finger extender bridge attached to the first and second finger extenders, the finger extender bridge slidably attached to the flexible outrigger.

4. The dynamic extension splint according to claim 1, wherein the platform includes a thumb extension portion disposed within the thumb jacket, the thumb extension portion cooperating with the thumb jacket to extend the person's thumb.

5. The dynamic extension splint according to claim 1, comprising an outrigger cushion pad attached to the outrigger at a location that prevents the outrigger from directly pressing against the dorsum of the hand.

6. The dynamic extension splint according to claim 1, wherein the finger extender is capable of keeping both the DIP and PIP joints in an open extended position.

7. A dynamic extension splint for biasing a person's fingers in an open position and having a low-profile configuration, comprising:
    a) a glove including a thumb jacket for positioning the person's thumb by covering and securing a portion of the thumb;
    b) a platform including an outrigger mount portion for attachment to the glove and configured to rest on the dorsum of the hand;
    c) a flexible outrigger for biasing at least one finger in an open position, the flexible outrigger mounted to the outrigger mount portion so that the outrigger extends between two adjacent fingers when the dynamic extension splint is being worn by the person, and the outrigger including a rod extending away from the outrigger mount portion parallel and proximate to the plane of the outrigger mount portion to provide the low-profile configuration of the dynamic extension splint; and
    d) at least one finger extender configured to surround a person's finger, the finger extender biasing the finger into an extended position and comprising an arcuate shape designed to fit snuggly around the person's finger.

8. The dynamic extension splint according to claim 7, comprising a finger extender bridge attached to a first and a second of the at least one finger extender, the finger extender bridge slidably attached to the flexible outrigger.

9. The dynamic extension splint according to claim 7, comprising an outrigger cushion pad attached to the outrigger at a location that prevents the outrigger from directly pressing against the dorsum of the hand.

10. The dynamic extension splint according to claim 7, wherein the platform includes a thumb extension portion for positioning within the thumb jacket and for cooperating with the thumb jacket to extend the person's thumb.

11. The dynamic extension splint according to claim 7, wherein the finger extender is sufficiently rigid to prevent an individual from curling his or her finger.

12. The dynamic extension splint according to claim 7, wherein the glove comprises a resilient material.

13. The dynamic extension splint according to claim 7, wherein the finger extender is an Oval-8 splint.

14. The dynamic extension splint according to claim 7, wherein the finger extender is capable of keeping both the DIP and PIP joints in an open extended position.

15. The dynamic extension splint according to claim 7, wherein the finger extender comprises:
    a) a warped circular saddle for supporting the palmar side of the finger, and
    b) a half ring bridge for supporting the dorsal side of the finger.

16. The dynamic extension splint according to claim 7, wherein the finger extender comprises:
    a) a cradle for supporting the palmar side of the finger, and
    b) a cradle connector for supporting the dorsal side of the finger.

17. A dynamic extension splint for biasing a person's fingers in an open position and having a low-profile configuration, comprising:
    a) a glove including a thumb jacket for positioning the person's thumb by covering and securing a portion of the thumb and including an outrigger mount portion for attachment to the glove;

b) a flexible outrigger for biasing at least two of a person's fingers in an open position, the flexible outrigger mounted to the outrigger mount portion and extending away from the outrigger mount portion parallel and proximate to the plane of the outrigger mount portion to provide the low-profile configuration of the dynamic extension splint; and c) two finger extenders each configured to surround a respective one of the person's index finger and long finger and biasing the fingers into an extended position, the finger extenders comprising an arcuate shape designed to fit snuggly around the person's fingers, wherein the finger extenders are sufficiently rigid to prevent a person from curling his index and long fingers while the person is wearing the dynamic extension splint.

18. The dynamic extension splint according to claim 17, comprising an outrigger cushion pad attached to the outrigger at a location that prevents the outrigger from directly pressing against the dorsum of the hand.

19. The dynamic extension splint according to claim 17, comprising a finger extender bridge attached to the first and second finger extenders, the finger extender bridge slidably attached to the flexible outrigger.

20. The dynamic extension splint according to claim 17, comprising a platform for attachment to the glove and configured to rest on the dorsum of the hand, the platform including a thumb extension portion for positioning within the thumb jacket and for cooperating with the thumb jacket to extend the person's thumb.

21. The dynamic extension splint according to claim 17, wherein the finger extenders are oval-8 splints.

22. The dynamic extension splint according to claim 17, wherein the finger extenders are capable of keeping both the DIP and PIP joints in an open extended position.

23. The dynamic extension splint according to claim 17, wherein the glove comprises a resilient material.

24. A dynamic extension splint for biasing a person's fingers in an open position and having a low-profile configuration, comprising:

a) a means for covering and supporting a person's hand including a thumb jacket for positioning the person's thumb by covering and securing a portion of the thumb;

b) an outrigger support means including an outrigger mount portion for attachment to the hand covering means and configured to rest on the dorsum of the hand;

c) an extension means for biasing at least two of the person's fingers in an extended open position and attached at a proximal end to the outrigger mount portion so that the outrigger is positioned between two adjacent fingers when the splint is being worn, the outrigger including:

i) a stop at the distal end of the outrigger; and ii) a rod extending away from the outrigger mount portion parallel and proximate to the plane of the outrigger mount portion to provide the low-profile configuration of the dynamic extension splint;

d) a first device for extending a finger including:

i) a warped circular saddle for supporting the palmar side of the finger, and ii) a half ring bridge for supporting the dorsal side of the finger; and e) a second device for extending a finger including:

i) a warped circular saddle for supporting the palmar side of the finger, and ii) a half ring bridge for supporting the dorsal side of the finger.

\* \* \* \* \*